US012565482B2

(12) United States Patent
Chen et al.

(10) Patent No.: US 12,565,482 B2
(45) Date of Patent: Mar. 3, 2026

(54) TEDIZOLID INTERMEDIATE AND EFFICIENT PREPARATION METHOD THEREOF

(71) Applicant: NANJING CHEMPION BIOTECHNOLOGY CO., LTD., Nanjing (CN)

(72) Inventors: Jian Chen, Nanjing (CN); Zhiqiang Liu, Nanjing (CN); Rong Gu, Nanjing (CN)

(73) Assignee: NANJING CHEMPION BIOTECHNOLOGY CO., LTD., Nanjing (CN)

( * ) Notice: Subject to any disclaimer, the term of this patent is extended or adjusted under 35 U.S.C. 154(b) by 896 days.

(21) Appl. No.: 17/828,059

(22) Filed: May 31, 2022

(65) Prior Publication Data

US 2023/0045135 A1 Feb. 9, 2023

Related U.S. Application Data

(63) Continuation of application No. PCT/CN2022/082429, filed on Mar. 23, 2022.

(30) Foreign Application Priority Data

Jul. 5, 2021 (CN) ......................... 202110754225.6

(51) Int. Cl.

*C07D 401/04* (2006.01)
*C07C 249/02* (2006.01)
*C07C 251/30* (2006.01)

(52) U.S. Cl.

CPC .......... *C07D 401/04* (2013.01); *C07C 249/02* (2013.01); *C07C 251/30* (2013.01)

(58) Field of Classification Search

CPC .... C07D 401/04; C07C 249/02; C07C 251/30
See application file for complete search history.

(56) References Cited

FOREIGN PATENT DOCUMENTS

| | | | |
|---|---|---|---|
| CN | 1894242 | A | 1/2007 |
| CN | 102177156 | A | 9/2011 |
| CN | 105367547 | A | 3/2016 |
| CN | 106220554 | A | 12/2016 |
| CN | 106632298 | A | 5/2017 |
| CN | 109715155 | A | 5/2019 |
| CN | 110804038 | A | 2/2020 |
| CN | 110938058 | A | 3/2020 |
| CN | 113354620 | A | 9/2021 |
| JP | 2001261653 | A | 9/2001 |
| WO | 2010042887 | A2 | 4/2010 |

OTHER PUBLICATIONS

Zhang Xue-Hui, et al., Synthesis of methyl 4-aryl-thiophene-2-carboxylate derivatives, Bull Acad Mil Med Sci, 2006, pp. 240-242, vol. 30, No. 3.

Luo Hairong, et al., Synthesis of the Key Intermediate Tedizolid Phosphate, Journal of Tongren University, 2017, pp. 4-6,11, vol. 19, No. 3.

*Primary Examiner* — Kamal A Saeed
(74) *Attorney, Agent, or Firm* — Bayramoglu Law Offices LLC

(57) ABSTRACT

The efficient preparation method of a tedizolid intermediate includes the following steps: 1) subjecting 2-fluoro-4-substituted phenylacetic acid to a reaction with a Vilsmeier reagent, and adding a resulting reaction solution to an MX aqueous solution for quenching to obtain an intermediate shown in formula (II); and 2) subjecting the intermediate shown in formula (II) obtained in step 1) and 1-(2-methyl-2H-tetrazol-5-yl)ethanone to one-pot synthesis in the presence of an alkali and an ammonia source to obtain the intermediate shown in formula (I). In this method, a pyridine ring of the key intermediate shown in formula (I) is obtained through a ring-closing reaction of the 1-(2-methyl-2H-tetrazol-5-yl)ethanone and a Vinamidinium salt, and a key methyltetrazolyl group is introduced into the structure, which successfully avoids the use of highly-toxic sodium cyanide and sodium azide, the use of expensive palladium catalyst, and the use of methylation with low selectivity.

14 Claims, 3 Drawing Sheets

TEDIZOLID INTERMEDIATE AND EFFICIENT PREPARATION METHOD THEREOF

CROSS REFERENCE TO THE RELATED APPLICATIONS

This application is the national phase entry of International Application No. PCT/CN2022/082429, filed on Mar. 23, 2022, which is based upon and claims priority to Chinese Patent Application No. 202110754225.6, filed on Jul. 5, 2021, the entire contents of which are incorporated herein by reference.

TECHNICAL FIELD

The present disclosure relates to the technical field of synthesis of pharmaceutical intermediates, and in particular to a tedizolid intermediate and an efficient preparation method thereof.

BACKGROUND

Tedizolid phosphate is a second-generation oxazolidinone antibiotic developed by Dong-A Pharmaceutical, which can be used for acute bacterial skin and skin structure infections caused by the following susceptible strains of Gram-positive bacteria: *Staphylococcus aureus* (*S. aureus*) (including methicillin-resistant and methicillin-susceptible strains), *Streptococcus pyogenes* (*S. pyogenes*), *Streptococcus lactis* (*S. lactis*), *Streptococcus anginosus* (*S. anginosus*) group (including *S. anginosus, Streptococcus intermedius* (*S. intermedius*), and *Streptococcus constellatus* (*S. constellatus*)), and *Enterococcus faecalis* (*E. faecalis*). Tedizolid phosphate is an upgraded product of linezolid, which shows a comparable clinical effect to linezolid, but leads to fewer adverse reactions than linezolid in the gastrointestinal tract and thrombocytopenia.

Currently, tedizolid

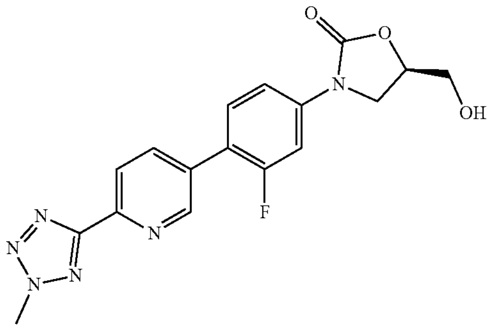 [SMILES: Cn1nnc(-c2ccc(-c3ccc(N4C[C@H](CO)OC4=O)cc3F)cn2)n1]

is synthesized mainly through the following routes.

Chinese patent CN200480037612 discloses the following synthetic route: benzyl 3-fluoro-4-bromophenyl carbamate is first prepared into a tin reagent, and then in the presence of a palladium catalyst, the tin reagent is subjected to a Stille reaction with 2-methyl-5-(5-bromopyridin-2-yl) tetrazole to obtain a tedizolid intermediate Ic. This synthetic route requires both the expensive palladium catalyst and the expensive tin reagent, and the tin reagent is very toxic and easily remains to cause great harm to the human body, which greatly limits the production of this route.

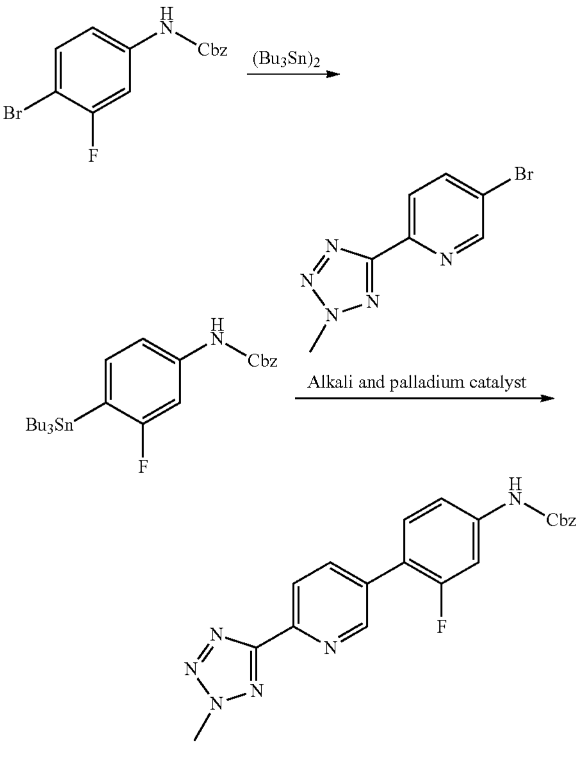

Ic

Chinese patent CN200908140144 discloses the following synthetic route: benzyl 3-fluoro-4-bromophenyl carbamate is first prepared into a borate intermediate under the action of butyllithium and triisopropyl borate, and then in the presence of a palladium catalyst, the borate intermediate is coupled with 2-methyl-5-(5-bromopyridin-2-yl)tetrazole to obtain a compound Ic. This synthetic route mainly has the following disadvantages: The reaction requires an ultra-low temperature (−78° C.) and special devices, and most companies do not enable these production conditions. Butyllithium is extremely flammable and thus is very dangerous in use. In addition, this synthetic route has a low yield, and uses the palladium catalyst, which greatly increases the production cost.

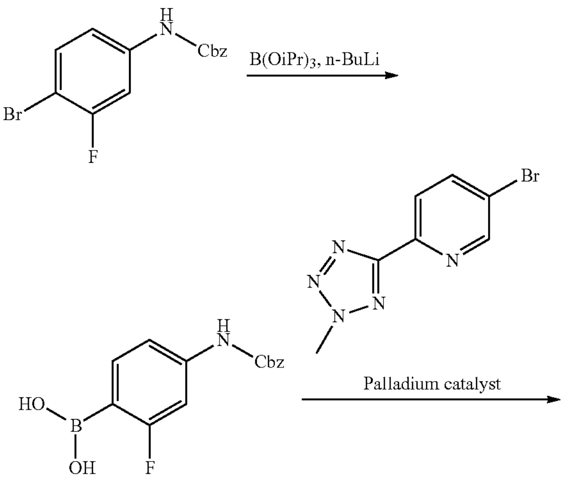

-continued

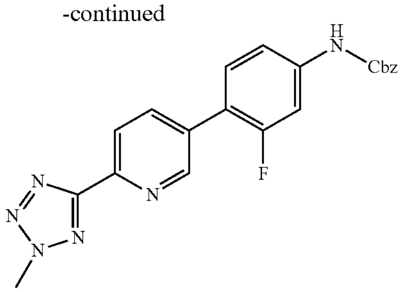

Ic

Chinese patent CN105367547A discloses the following synthetic route: 2-methyl-5-(5-bromopyridin-2-yl) tetrazole is prepared into a borate intermediate under the action of a palladium catalyst and bis(pinacolato)diboron, and the borate can be directly added to benzyl 3-fluoro-4-bromophenyl carbamate without separation for one-pot synthesis to obtain a product Ic. This method avoids the use of toxic tin reagent and extremely-flammable butyllithium, and does not require an ultra-low temperature. However, the use of the palladium catalyst still makes this route expensive.

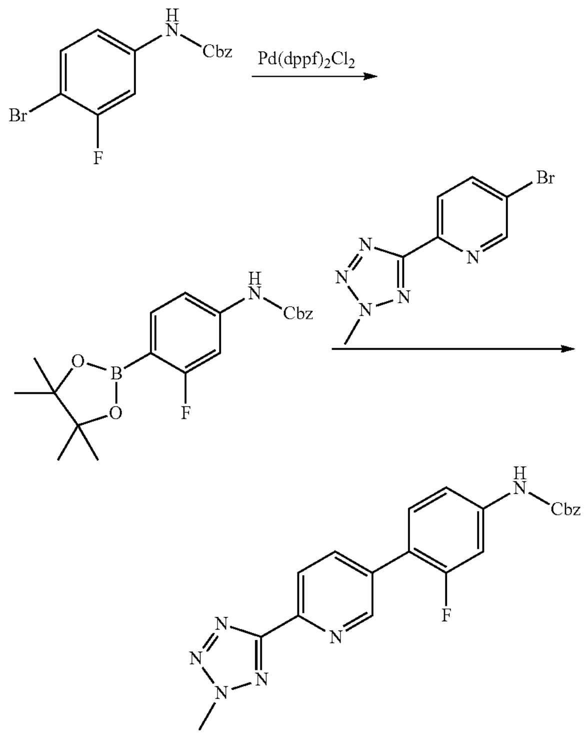

Ic

Chinese patent CN106632298A discloses the following synthetic route: 2-methyl-5-(5-bromopyridin-2-yl) tetrazole is prepared into a borate intermediate under the action of a palladium catalyst and bis(pinacolato)diboron, then the borate intermediate is subjected to a Suzuki coupling reaction with 3-fluoro-4-bromoaniline, and after the coupling, amino in the product is converted into a halogen, and then the product is subjected to a coupling reaction with chiral oxazoline ketone to obtain a target product. This method still involves a multi-step metal-catalyzed coupling reaction, making it difficult to reduce the production cost.

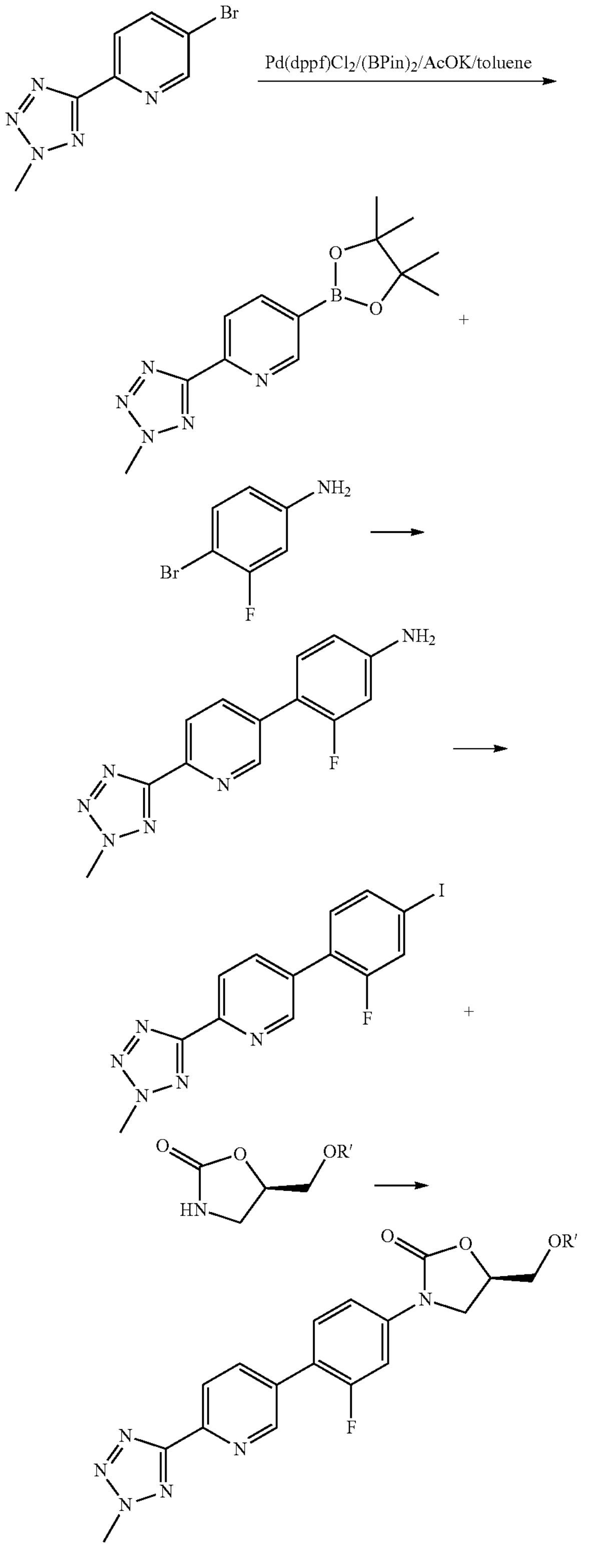

In addition, the above four routes inevitably use the intermediate 2-methyl-5-(5-bromopyridin-2-yl) tetrazole, and a current route for synthesizing this intermediate is as follows: in the presence of sodium cyanide and cuprous cyanide, 2,5-dibromopyridine is prepared into 2-cyano-5-bromopyridine, then 2-cyano-5-bromopyridine is subjected to a ring-closing reaction with sodium azide to obtain a tetrazole intermediate, and the tetrazole intermediate is then methylated to obtain the intermediate 2-methyl-5-(5-bromopyridin-2-yl)tetrazole. The synthetic route of this intermediate uses the highly-toxic sodium cyanide, which results in a high potential risk and is unfavorable for industrial production; and the methylation reaction has a yield only of about 50%, which greatly increases the cost.

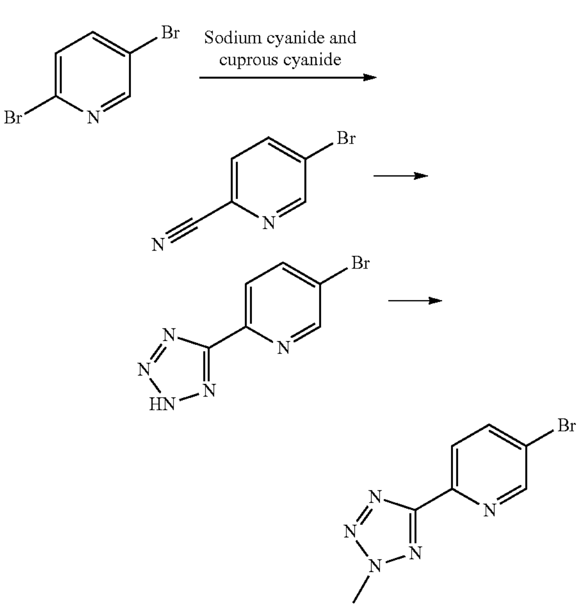

SUMMARY

The present disclosure is intended to develop a method for preparing a tedizolid intermediate with high efficiency, safety, and low cost, which can avoid the use of sodium cyanide, sodium azide, and a palladium catalyst, and is suitable for large-scale industrial production.

To achieve the above objective, the present disclosure adopts the following technical solutions:

An efficient preparation method of a tedizolid intermediate is provided, where the intermediate is shown in formula (I):

I

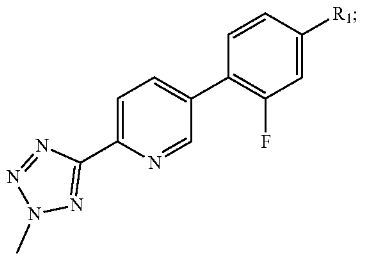

and the efficient preparation method includes the following steps:

1) subjecting 2-fluoro-4-substituted phenylacetic acid to a reaction with a Vilsmeier reagent, and adding a resulting reaction solution to an MX aqueous solution for quenching to obtain an intermediate shown in formula (II):

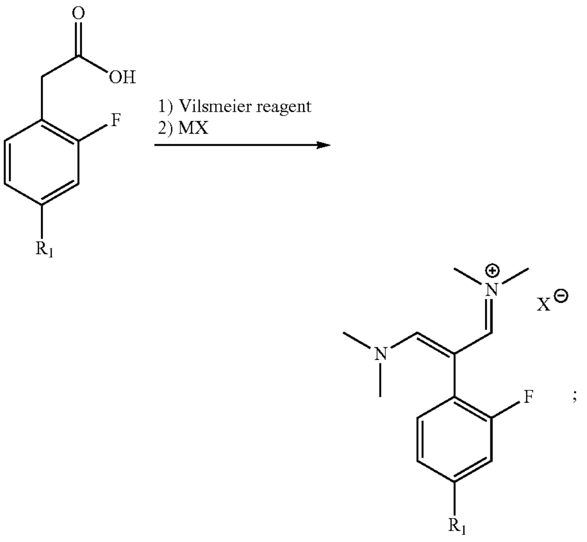

II and 2) subjecting the intermediate shown in formula (II) obtained in step 1) and 1-(2-methyl-2H-tetrazol-5-yl) ethanone to one-pot synthesis in the presence of an alkali and an ammonia source to obtain the intermediate shown in formula (I):

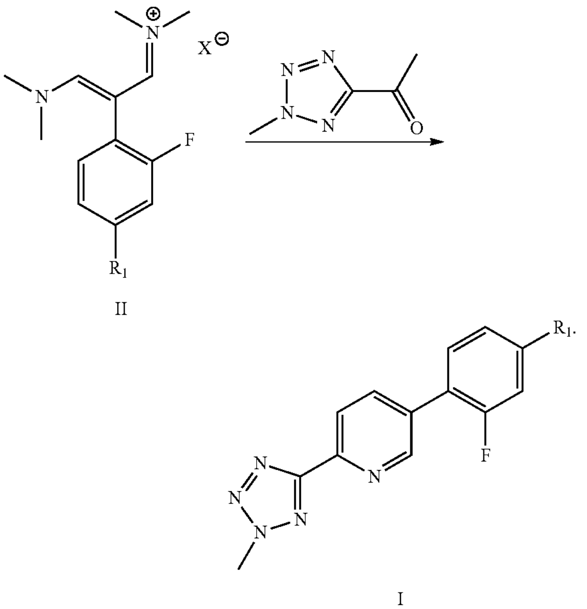

II

I

Further, in step 1), $R_1$ may be nitro; benzyloxycarbonylamino; chlorine; bromine; iodine; sulfonyl such as trifluorosulfonyloxy, methanesulfonyloxy, benzenesulfonyloxy, or p-toluenesulfonyloxy; or carboxylate.

Further, in step 1), the Vilsmeier reagent may be a combination of N,N-dimethylformamide (DMF) and phosphorus oxychloride, or DMF and oxalyl chloride, or DMF and thionyl chloride.

Further, in step 1), the MX may be sodium tetrafluoroborate, potassium tetrafluoroborate, sodium perchlorate, sodium hexafluorophosphate, or potassium hexafluorophosphate; and $X^{\ominus}$ may be a tetrafluoroborate ion, a perchlorate ion, or a hexafluorophosphate ion.

Further, in step 1), an amount of the MX may be 1 to 3 and preferably 1.5 equivalents of an amount of the 2-fluoro-4-substituted phenylacetic acid.

Further, the reaction in step 1) may be conducted at 0° C. to 100° C. and preferably at 25° C. to 90° C.

Further, the alkali in step 2) may be potassium tert-butoxide, sodium tert-butoxide, sodium methoxide, sodium ethoxide, lithium N,N-diisopropylamide, sodium hydride, sodium amide, lithium hexamethyldisilazide (LiHMDS), sodium hexamethyldisilazide (NaHMDS), potassium hexamethyldisilazide (KHMDS), 1,8-diazadispiro[5.4.0]undec-7-ene, 1,1,3,3-tetramethylguanidine, N,N-diisopropylethylamine (DIPEA), triethylamine (TEA), pyrrolidine, piperidine, or morpholine; may preferably be potassium tert-butoxide, lithium N,N-diisopropylamide, 1,8-diazadispiro[5.4.0]undec-7-ene, 1,1,3,3-tetramethylguanidine, or NaHMDS; and may more preferably be potassium tert-butoxide.

Further, a solvent used in step 2) may be selected from the group consisting of tetrahydrofuran (THF), dioxane, DMF, dimethyl sulfoxide (DMSO), N-methylpyrrolidone (NMP), N,N-dimethylacetamide (DMAC), and acetonitrile; and may preferably be THF.

Further, in step 2), an amount of the 1-(2-methyl-2H-tetrazol-5-yl)ethanone may be 0.5 to 2.0 and preferably 1.5 equivalents of an amount of the intermediate shown in formula (II).

Further, the ammonia source in step 2) may be ammonia water, a solution of ammonia in methanol, ammonium acetate, ammonium chloride, ammonium sulfate, ammonium carbonate, or ammonium bicarbonate; and may preferably ammonium acetate.

Further, in step 2), an amount of the ammonia source may be 5.0 to 10.0 and preferably 5.0 equivalents of the amount of the intermediate shown in formula (II).

Further, the one-pot synthesis in step 2) may be conducted at −10° C. to 100° C.

In some embodiments of the method, $R_1$ in the intermediate shown in formula (I) may be nitro, Ia

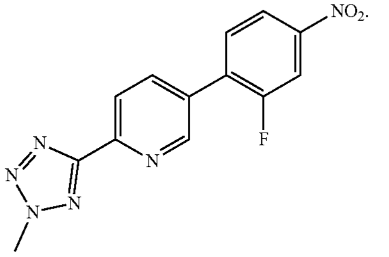

In some embodiments of the method, the intermediate shown in formula (Ia) may be reduced by a reducing agent to obtain a compound shown in formula (Ib):

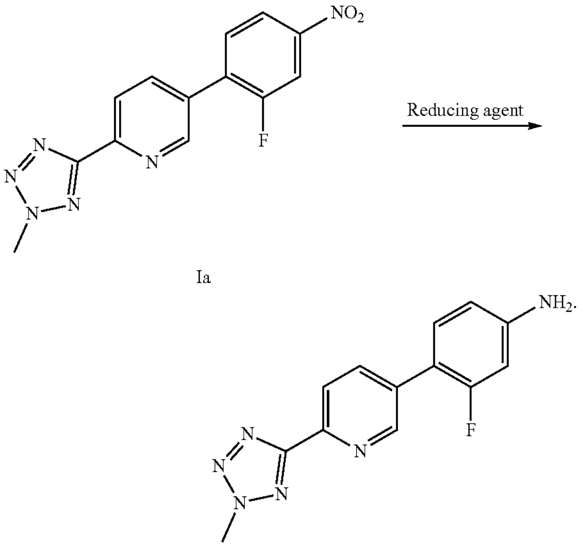

Ia

Ib

The reducing agent in this step may be a combination of a zinc powder and ammonium chloride, a combination of a zinc powder and acetic acid, sodium thiosulfate, sodium hydrosulfite, or the like; and when an atmospheric pressure or pressurized hydrogenation reaction is conducted in the presence of a metal catalyst such as Raney nickel, palladium on carbon, or palladium hydroxide on carbon, the combination of the zinc powder with ammonium chloride or acetic acid may be preferred.

Further, the intermediate shown in formula (Ib) obtained in the above step may react with benzyl chloroformate to obtain the compound shown in formula (Ic):

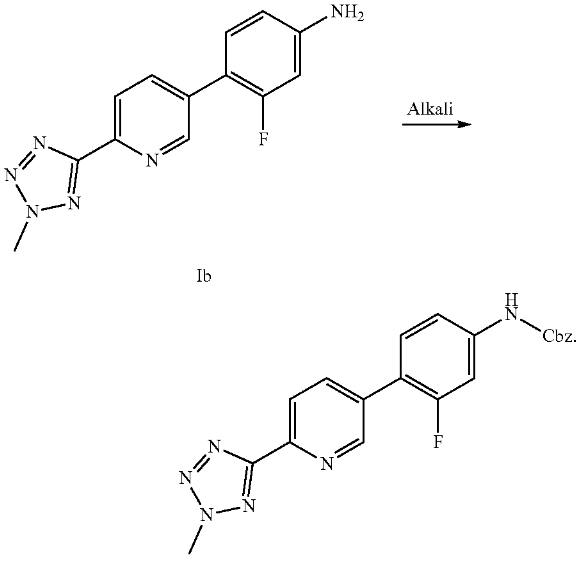

Ib

Ic

The alkali in the above step may be sodium bicarbonate, sodium carbonate, potassium carbonate, sodium phosphate, potassium phosphate, 1,8-diazadispiro[5.4.0]undec-7-ene, DIPEA, or TEA.

In some embodiments of the method, $R_1$ in the intermediate shown in formula (I) may be carboxylate,

III

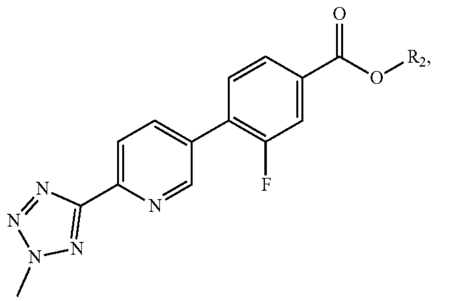

where $R_2$ may be methyl, ethyl, tert-butyl, and benzyl.

In some embodiments of the method, the intermediate shown in formula (III) can be subjected to hydrolysis and Curtius rearrangement to obtain an intermediate shown in formula (Id):

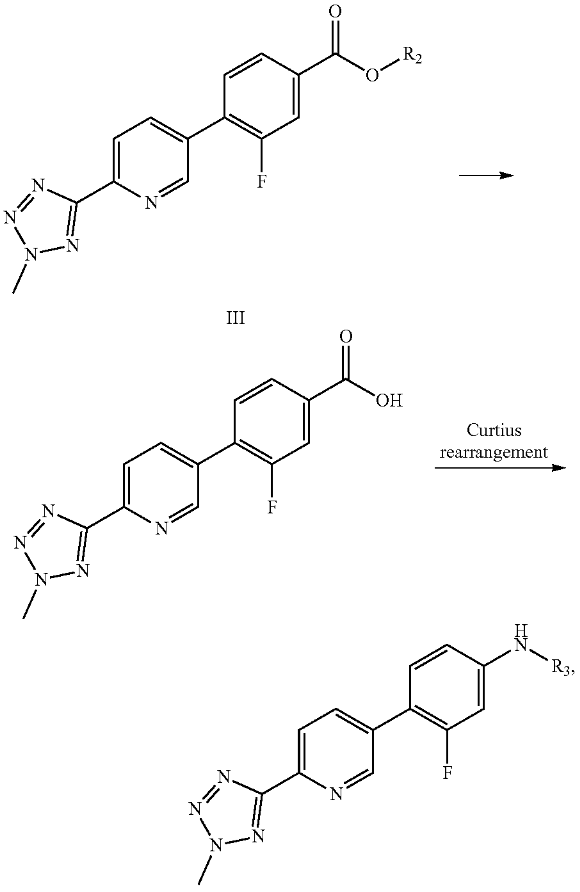

III

Id where $R_3$ is hydrogen, tert-butoxycarbonyl, or benzyloxycarbonyl.

An intermediate shown in formula II prepared by the efficient preparation method of a tedizolid intermediate is provided.

The technical solutions in the present disclosure have the following beneficial effects:

The present disclosure provides a novel method for efficiently preparing the tedizolid intermediate. In this method, a pyridine ring of the key intermediate shown in formula (I) is obtained through a ring-closing reaction of the 1-(2-methyl-2H-tetrazol-5-yl)ethanone and a Vinamidinium salt, and a key methyltetrazolyl group is introduced into the structure, which successfully avoids the use of highly-toxic sodium cyanide and sodium azide, the use of expensive palladium catalyst, and the use of methylation with low selectivity.

The preparation method of the present disclosure has the characteristics of simple process, concise steps, mild reaction conditions, safe production, and low cost, and thus is suitable for industrial production.

DETAILED DESCRIPTION OF THE EMBODIMENTS

Figure 1:
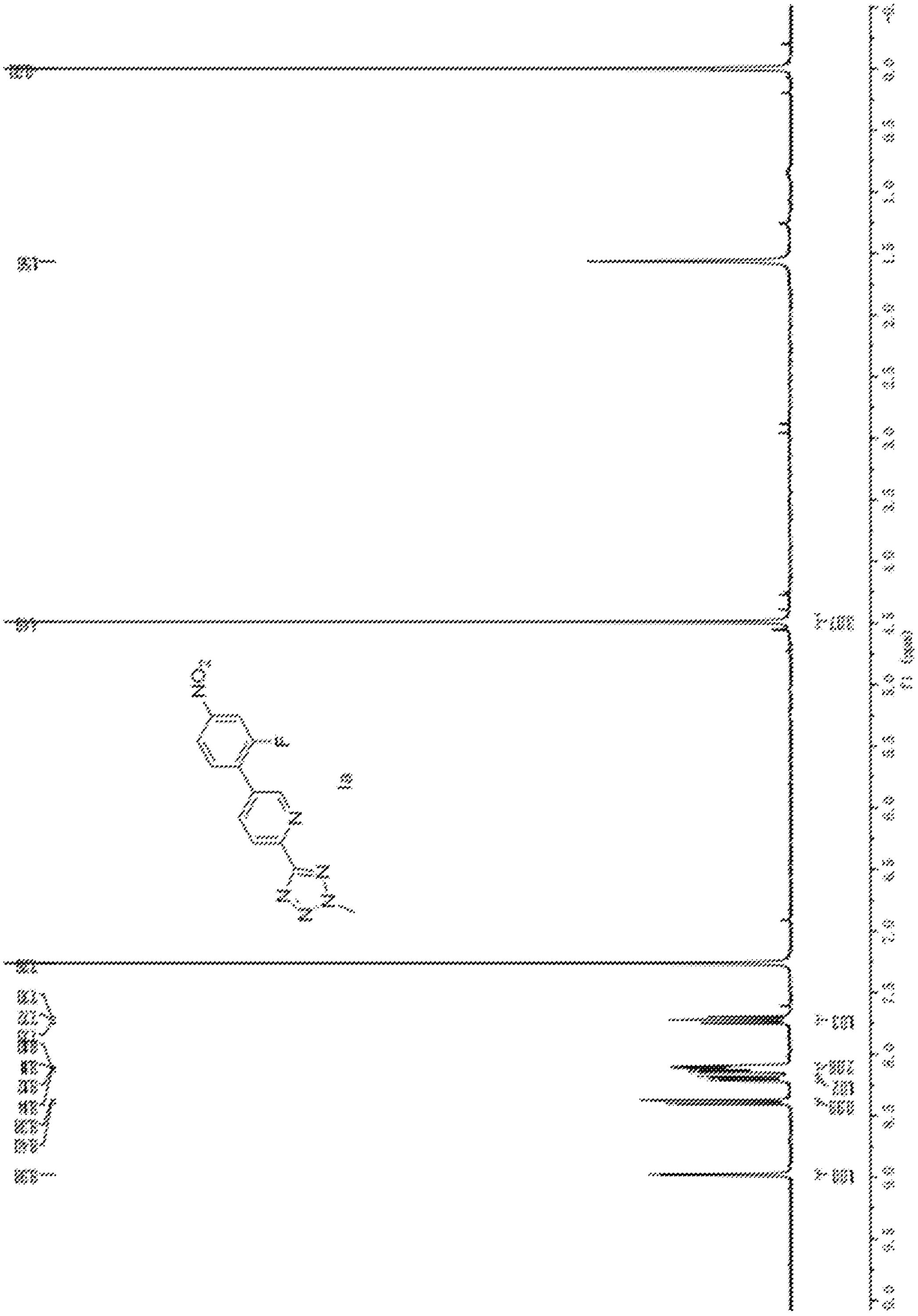
FIG. 1 is a proton nuclear magnetic resonance (HNMR) spectrum of formula Ia in the present disclosure.

For better understanding the usage of the present disclosure, the following specific examples will be illustrated to describe the technical solutions clearly and completely. Apparently, the described examples are merely some rather than all of the examples of the present disclosure. All other examples obtained by a person of ordinary skill in the art based on the examples of the present disclosure without creative efforts shall fall within the protection scope of the present disclosure.

The raw materials and devices used in the specific embodiments of the present disclosure are all known products, and are all commercially available products, which, for example, can be purchased from Beijing J&K Scientific Ltd., Shanghai Shaoyuan Co., Ltd., and the like.

Example 1

Preparation of (E)-N-(3-(dimethylamino)-2-(2-fluoro-4-nitrophenyl) allylidene)-N-methylmethylaminoperchlorate

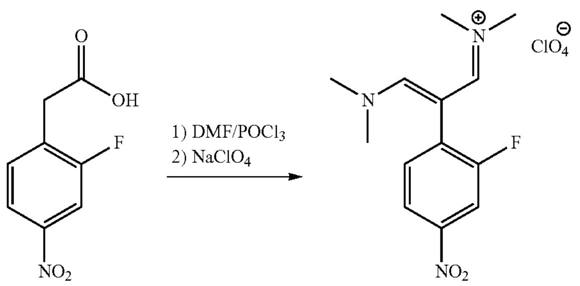

SMA1 IIa

Phosphorus oxychloride (191.7 g, 1.25 mol) was added dropwise to DMF (600 mL), where a temperature was controlled at 10° C. to 30° C. and the dropwise addition was conducted for 30 min; a reaction was conducted at room temperature for 30 min; then (2-Fluoro-4-nitrophenyl)acetic acid (99.5 g, 0.5 mol) was added, a resulting mixture was heated to 85° C. to allow a reaction for 3 hours, and a resulting reaction solution was cooled to room temperature, poured into a solution of sodium perchlorate (91.5 g, 0.75 mol) in water (1.2 L) for quenching, and stirred at room temperature for 1 hour; and a resulting mixture was filtered, and a resulting filter cake was washed with water (200 mL) and then dried to obtain a compound IIa (165 g, 90%), which was a khaki solid. 1HNMR (400 MHZ, DMSO) δ8.22-8.25 (dd, 1H), 8.14-8.17 (dd, 1H), v8.14-8.17 (dd, 1H), 7.89 (s, 2H), 7.66-7.71 (m, 1H), 2.53 (s, 6H).

Example 2

Preparation of 5-(2-fluoro-4-nitrophenyl)-2-(2-methyl-2H-tetrazol-5-yl) pyridine

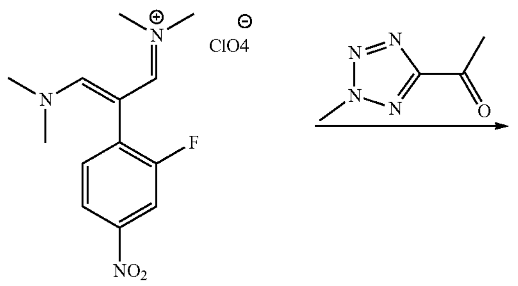

IIa

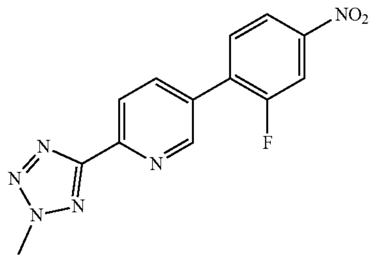

Ia

Method 1:

The compound IIa (15 g, 40 mmol) was added to THF (150 mL), and then 1-(2-methyl-2H-tetrazol-5-yl) ethanone (7.5 g, 60 mmol) was added; a resulting reaction solution was cooled to −10° C., then NaHMDS (2 M, 30 mL, 60 mmol) was slowly added dropwise, and then a reaction was conducted at −10° C. for 10 min; ammonium acetate (15.4 g, 0.2 mol) and water (45 mL) were then added, and a resulting mixture was heated to 70° C. to allow a reaction for 18 hours; when LCMS showed that the reaction was completed, a resulting reaction solution was cooled to room temperature, ethyl acetate (75 mL) was added for extraction, and a resulting organic phase was subjected to vacuum distillation to obtain a crude product; and the crude product was slurried with n-hexane (75 mL) and ethyl acetate (30 mL) and filtered, and a resulting filter cake was dried to obtain a compound Ia (6.36 g, 53%), which was a khaki solid. 1HNMR (400 MHZ, CDCl3) δ8.98 (s, 1H), 8.38-8.40 (d, 1H), 8.18-8.22 (dd, 1H), 8.10-8.14 (m, 2H), 7.61-7.75 (m, 1H), 4.49 (s, 3H), as shown in FIG. 1.

Method 2:

The compound IIa (15 g, 40 mmol) was added to THF (150 mL), and then 1-(2-methyl-2H-tetrazol-5-yl) ethanone (7.5 g, 60 mmol) was added; a resulting reaction solution was cooled to 0° C., then 1,1,3,3-tetramethylguanidine (9.2 g, 80 mmol) was added, and then a reaction was conducted at 0° C. for 1 hour; ammonium acetate (15.4 g, 0.2 mol) and water (45 mL) were then added, and a resulting mixture was heated to 70° C. to allow a reaction for 18 hours; when LCMS showed that the reaction was completed, a resulting reaction solution was cooled to room temperature, ethyl acetate (75 mL) was added for extraction, and a resulting organic phase was subjected to vacuum distillation to obtain a crude product; and the crude product was slurried with n-hexane (75 mL) and ethyl acetate (30 mL) and filtered, and a resulting filter cake was dried to obtain a compound Ia (5.08 g, 42.3%), which was a khaki solid. 1HNMR (400 MHZ, CDCl3) δ8.98 (s, 1H), 8.38-8.40 (d, 1H), 8.18-8.22 (dd, 1H), 8.10-8.14 (m, 2H), 7.61-7.75 (m, 1H), 4.49 (s, 3H).

Method 3:

The compound IIa (15 g, 40 mmol) was added to THF (150 mL), and then 1-(2-methyl-2H-tetrazol-5-yl) ethanone (7.5 g, 60 mmol) was added; a resulting reaction solution was cooled to −10° C., then potassium tert-butoxide (9 g, 80 mmol) was added, and then a reaction was conducted at −10° C. for 1 hour; ammonium acetate (15.4 g, 0.2 mol) and water (45 mL) were then added, and a resulting mixture was heated to 70° C. to allow a reaction for 18 hours; when LCMS showed that the reaction was completed, a resulting reaction solution was cooled to room temperature, ethyl acetate (75 mL) was added for extraction, and a resulting organic phase was subjected to vacuum distillation to obtain a crude product; and the crude product was slurried with n-hexane (75 mL) and ethyl acetate (30 mL) and filtered, and a resulting filter cake was dried to obtain a compound Ia (7.5 g, 62.5%), which was a khaki solid. 1HNMR (400 MHZ, CDCl3) δ8.98 (s, 1H), 8.38-8.40 (d, 1H), 8.18-8.22 (dd, 1H), 8.10-8.14 (m, 2H), 7.61-7.75 (m, 1H), 4.49 (s, 3H), as shown in FIG. 1.

Example 3

Preparation of 3-fluoro-4-(6-(2-methyl-2H-tetrazol-5-yl)pyridin-3-yl)aniline

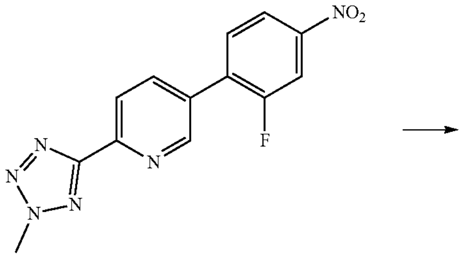

Ia

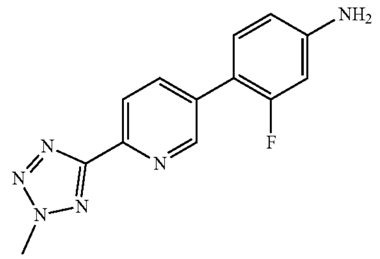

Ib

Figure 2:
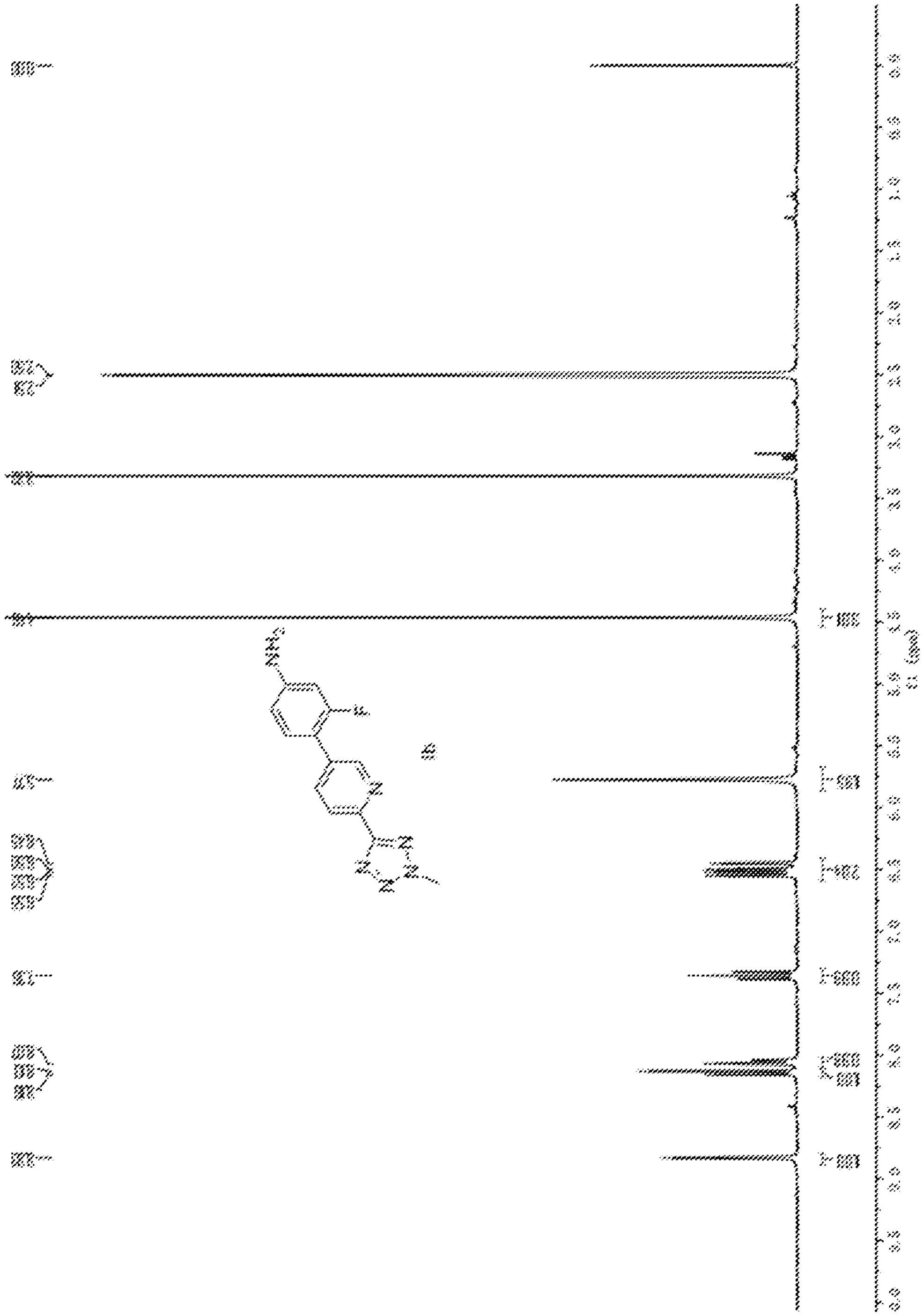
FIG. 2 is an HNMR spectrum of formula Ib in the present disclosure.

The compound Ia (2 g, 6.67 mmol) was added to ethanol (30 mL), then saturated ammonium chloride (10 mL) and a zinc powder (4.3 g, 66.7 mol) were added, and a resulting mixture was heated to 80° C. to allow a reaction for 2 hours; when LCMS showed that the reaction was completed, a resulting reaction solution was filtered, and a resulting filtrate was subjected to vacuum concentration to remove ethanol and then filtered; and a resulting filter cake was rinsed with water (4 mL) and then was dried to obtain a compound Ib (1.62 g, 90%), which was an off-white solid. 1HNMR (400 MHZ, DMSO) δ8.83 (s, 1H), 8.07-8.16 (m, 2H), 7.33-7.39 (m, 1H), 6.44-6.55 (m, 2H), 5.77 (s, 2H), 4.46 (s, 3H), as shown in FIG. 2.

Example 4

Preparation of benzyl (3-fluoro-4-(6-(2-methyl-2H-tetrazol-5-yl)pyridin-3-yl) phenyl)carbamate

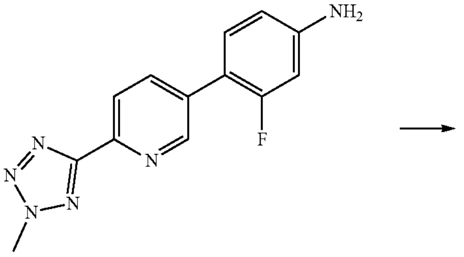

Ib

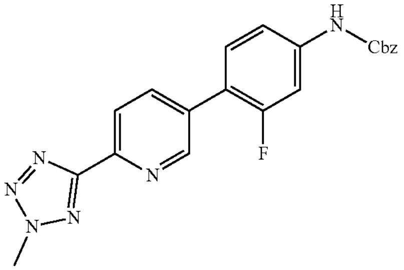

Ic

Figure 3:
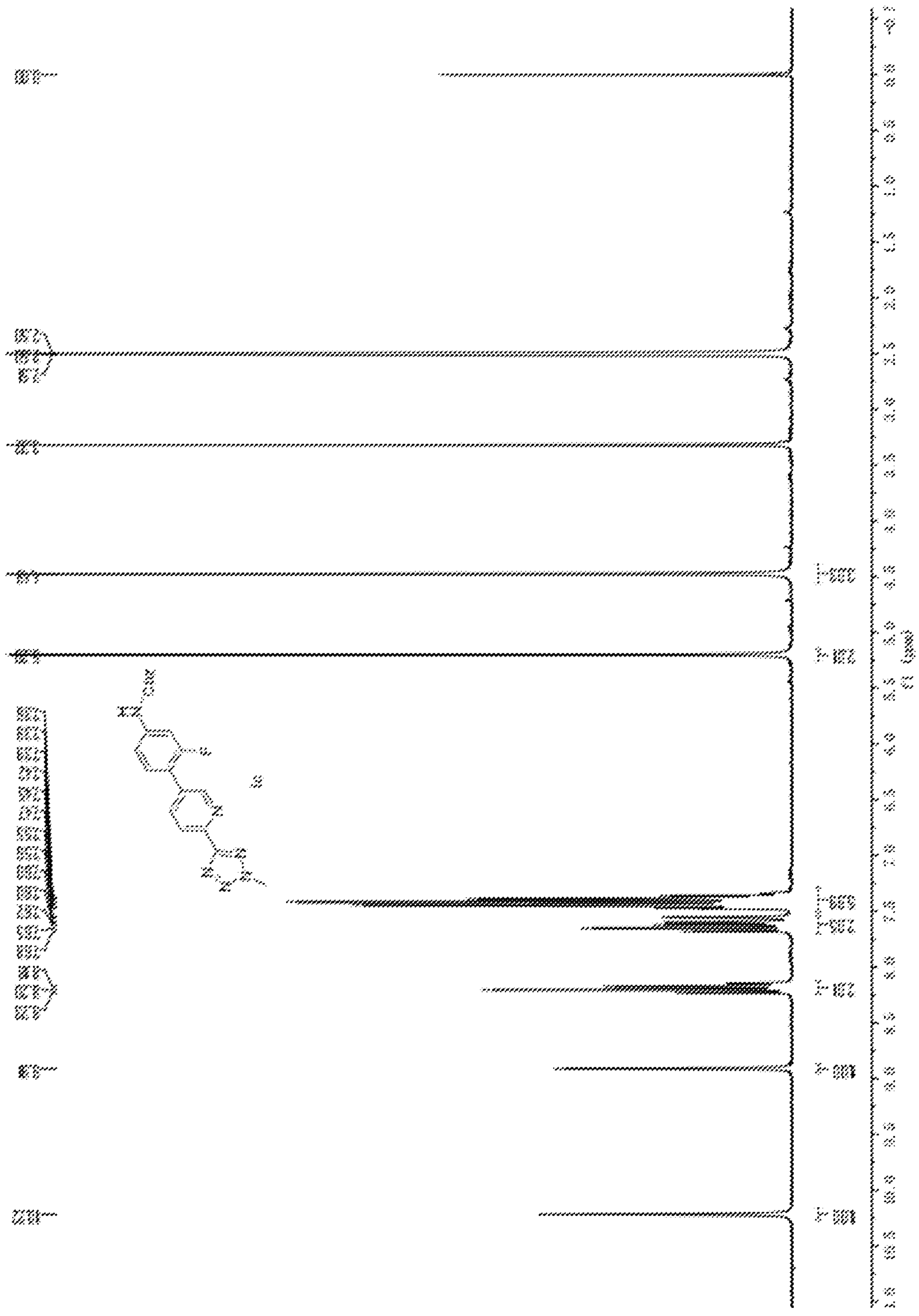
FIG. 3 is an HNMR spectrum of formula Ic in the present disclosure.

The compound Ib (1 g, 3.7 mmol) was added to THF (10 mL), then sodium bicarbonate (0.93 g, 11.1 mmol) and benzyl chloroformate (0.95 g, 5.55 mmol) were added, and a reaction was conducted at room temperature for 2 hours; when LCMS showed that the reaction was completed, water (10 mL) was added, and then extraction was conducted twice with ethyl acetate (20 mL); resulting organic phases were combined, dried over anhydrous sodium sulfate, filtered, and subjected to vacuum concentration to obtain a crude product; and the crude product was slurried with ethyl acetate (3 mL) and n-hexane (9 mL) and then filtered, and a resulting filter cake was dried to obtain a compound Ic (1.35 g, 90%), which was an off-white solid. 1HNMR (400 MHZ, DMSO) δ10.22 (s, 1H), 8.91 (s, 1H), 8.15-8.23 (m, 2H), 7.55-7.65 (m, 2H), 7.36-7.47 (m, 6H), 5.20 (s, 2H), 4.48 (s, 3H), as shown in FIG. 3.

Example 5

Preparation of (E)-N-(3-(dimethylamino)-2-(2-fluoro-4-iodo)allylidene)-N-methylmethylaminoperchlorate

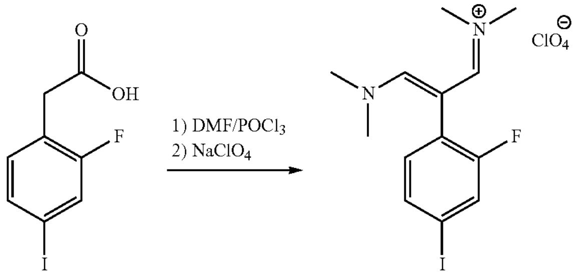

SMA2 IIb

Phosphorus oxychloride (6.9 g, 45 mmol) was added dropwise to DMF (30 mL), where a temperature was controlled at 10° C. to 30° C. and the dropwise addition was conducted for 30 min; a reaction was conducted at room temperature for 30 min; then (2-Fluoro-4-nitrophenyl)acetic acid (5 g, 18 mmol) was added, a resulting mixture was heated to 85° C. to allow a reaction for 3 hours, and a resulting reaction solution was cooled to room temperature, poured into a solution of sodium perchlorate (3.3 g, 27 mmol) in water (60 mL) for quenching, and stirred at room temperature for 1 hour; and a resulting mixture was filtered, and a resulting filter cake was washed with water (10 mL) and then dried to obtain a compound IIb (7.1 g, 89%), which was a khaki solid.

Example 6

Preparation of 5-(2-fluoro-4-iodophenyl)-2-(2-methyl-2H-tetrazol-5-yl) pyridine

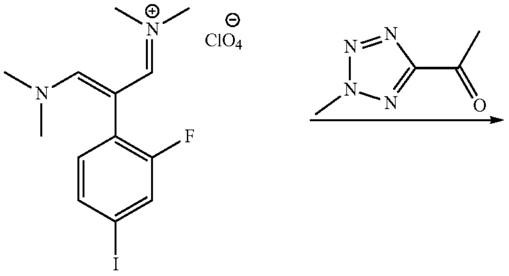

IIb

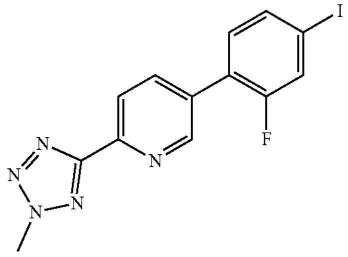

Ie

The compound IIb (5 g, 11.2 mmol) was added to THF (50 mL), and then 1-(2-methyl-2H-tetrazol-5-yl) ethanone (2.1 g, 16.8 mmol) was added; a resulting reaction solution was cooled to −10° C., then NaHMDS (2 M, 8.4 mL, 16.8 mmol) was slowly added dropwise, and then a reaction was conducted at −10° C. for 10 min; ammonium acetate (4.3 g, 56 mmol) and water (15 mL) were then added, and a resulting mixture was heated to 70° C. to allow a reaction for 18 hours; when LCMS showed that the reaction was completed, a resulting reaction solution was cooled to room temperature, ethyl acetate (20 mL) was added for extraction, and a resulting organic phase was subjected to vacuum distillation to obtain a crude product; and the crude product was slurried with n-hexane (20 mL) and ethyl acetate (10 mL) and filtered, and a resulting filter cake was dried to obtain a compound Ie (2.1 g, 49%), which was a yellow-brown solid. 1HNMR (400 MHZ, CDCl3) δ8.89 (s, 1H), 8.32 (d, 1H), 8.07 (d, 1H), 7.70 (m, 1H), 7.56 (dd, 1H), 7.49 (d, 1H), 4.45 (s, 3H).

Example 7

Preparation of (E)-N-(3-(dimethylamino)-2-(2-fluoro-4-methoxycarbonyl) allylidene)-N-methylm-ethylaminoperchlorate

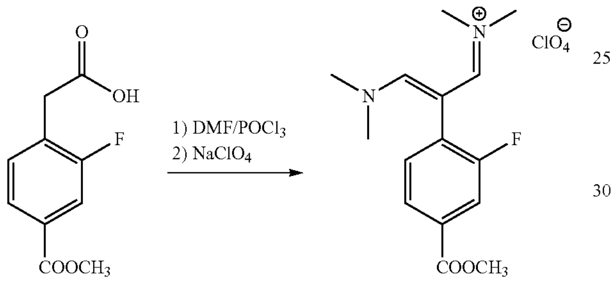

SMA3 IIc

Phosphorus oxychloride (19.2 g, 0.125 mol) was added dropwise to DMF (60 mL), where a temperature was controlled at 10° C. to 30° C. and the dropwise addition was conducted for 30 min; a reaction was conducted at room temperature for 30 min; then (2-Fluoro-4-nitrophenyl)acetic acid (10.6 g, 50 mmol) was added, a resulting mixture was heated to 85° C. to allow a reaction for 3 hours, and a resulting reaction solution was cooled to room temperature, poured into a solution of sodium perchlorate (9.2 g, 75 mmol) in water (150 mL) for quenching, and stirred at room temperature for 1 hour; and a resulting mixture was filtered, and a resulting filter cake was washed with water (20 mL) and then dried to obtain a compound IIc (14.0 g, 74%), which would be directly used in the next step.

Example 8

Preparation of 5-(2-fluoro-4-methoxycarbonylphenyl)-2-(2-methyl-2H-tetrazol-5-yl)pyridine

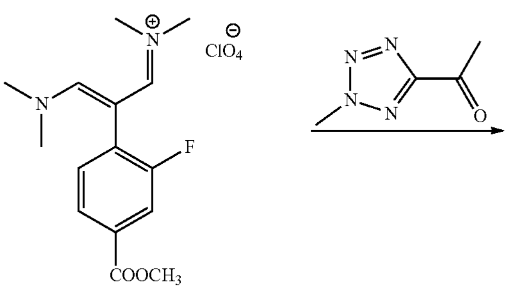

IIc

-continued

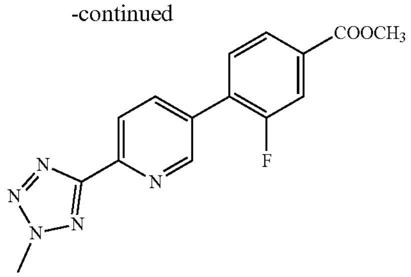

IIIa

The compound IIc (10 g, 26.4 mmol) was added to THF (100 mL), and then 1-(2-methyl-2H-tetrazol-5-yl) ethanone (5 g, 40 mmol) was added; a resulting reaction solution was cooled to −10° C., then NaHMDS (2 M, 20 mL, 40 mmol) was slowly added dropwise, and then a reaction was conducted at −10° C. for 10 min; ammonium acetate (10.2 g, 0.132 mol) and water (30 mL) were then added, and a resulting mixture was heated to 70° C. to allow a reaction for 18 hours; when LCMS showed that the reaction was completed, a resulting reaction solution was cooled to room temperature, ethyl acetate (50 mL) was added for extraction, and a resulting organic phase was subjected to vacuum distillation to obtain a crude product; and the crude product was slurried with n-hexane (50 mL) and ethyl acetate (20 mL) and filtered, and a resulting filter cake was dried to obtain a compound Ma (3.06 g, 37%), which would be directly used in the next step.

Example 9

Preparation of benzyl (3-fluoro-4-(6-(2-methyl-2H-tetrazol-5-yl)pyridin-3-yl) phenyl)carbamate

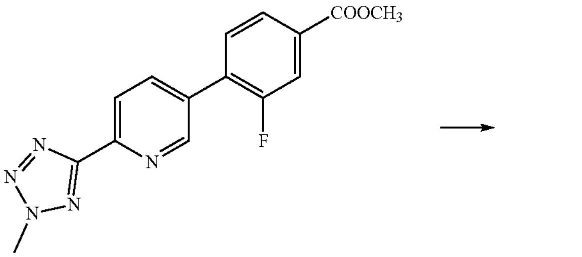

IIIa

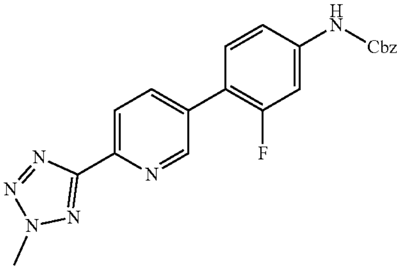

Ic

The compound Ma (3 g, 9.6 mmol) was added to a mixture of methanol (10 mL) and water (10 mL), then lithium hydroxide monohydrate (0.8 g, 19.2 mmol) was added, and a resulting mixture was stirred overnight at room temperature; when it was determined by TLC that the reaction was completed, a pH of a resulting reaction solution was adjusted to 2 to 3 with a 1 N aqueous hydrochloric acid solution, and a resulting solid was filtered out, washed with water (50 mL), subjected to suction filtration, and dried under reduced pressure to obtain crude carboxylic acid (2.9 g).

The crude carboxylic acid (2.9 g) was dissolved in toluene (30 mL), then TEA (2 g, 19.8 mmol) and DPPA (3.2 g, 11.6 mmol) were added, and a resulting mixture was heated to 100° C. to allow a reaction for 7 hours; then benzyl alcohol (2.1 g, 19.4 mmol) was added, and a resulting mixture was continuously stirred for 8 hours; when it was monitored by TLC that the reaction was completed, toluene was removed under reduced pressure, ethyl acetate (20 mL) and water (20 mL) were added, and a resulting aqueous phase was subjected to extraction with ethyl acetate (10 mL×2); resulting organic phases were combined, dried over anhydrous sodium sulfate, and spin-dried under reduced pressure to obtain a crude product; and the crude product was purified by a silica gel column with petroleum ether:ethyl acetate (1:1) to obtain a compound Ic (1.88 g, 48%).

The above are merely preferred examples of the present disclosure, and are not intended to limit the present disclosure in any form. Although the present disclosure has been disclosed by the above examples, the examples are not intended to limit the present disclosure. Any person skilled in the art may make some changes or modifications to obtain equivalent examples with equivalent changes using the method and technical content disclosed above without departing from the scope of the technical solution of the present disclosure. Any simple modification, equivalent change, and modification made to the above examples according to the technical essence of the present disclosure without departing from the content of the technical solution of the present disclosure shall fall within the scope of the technical solution of the present disclosure.

What is claimed is:

1. A method of preparing a tedizolid intermediate of formula (I):

I

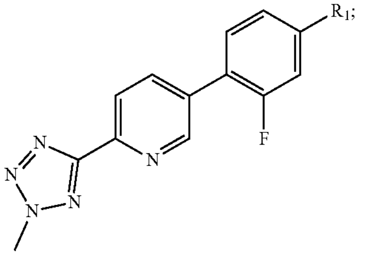

wherein $R_1$ is selected from the group consisting of: nitro, benzyloxycarbonylamino, chlorine, bromine, iodine, trifluorosulfonyloxy, methanesulfonyloxy, benzenesulfonyloxy, p-toluenesulfonyloxy, and carboxylate;

the method comprising the following steps:

1) Subjecting 2-fluoro-4-substituted phenylacetic acid to a reaction with a Vilsmeier reagent, and adding a resulting reaction solution to an MX aqueous solution for quenching to obtain an intermediate shown in formula (II):

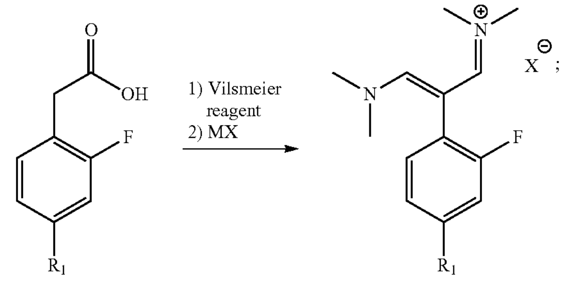

II wherein the MX is selected from the group consisting of: sodium tetrafluoroborate, potassium tetrafluoroborate, sodium perchlorate, sodium hexafluorophosphate, and potassium hexafluorophosphate, and $X^{\ominus}$ is selected from the group consisting of: a tetrafluoroborate ion, a perchlorate ion, and a hexafluorophosphate ion; and 2) subjecting the intermediate shown in formula (II) obtained in step 1) and 1-(2-methyl-2H-tetrazol-5-yl) ethanone to a one-pot synthesis in the presence of an alkali and an ammonia source to obtain the tedizolid intermediate shown in formula (I):

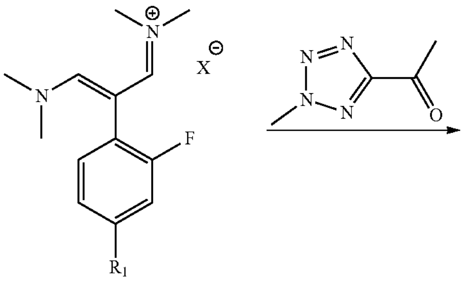

II

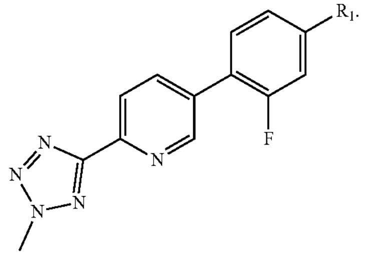

I

2. The method according to claim 1, wherein in step 1), the Vilsmeier reagent is a combination of: N,N-dimethylformamide (DMF) and phosphorus oxychloride, DMF and oxalyl chloride, or DMF and thionyl chloride.

3. The method according to claim 1, wherein in step 1), an amount of the MX is 1 to 3 equivalents of an amount of the 2-fluoro-4-substituted phenylacetic acid.

4. The method according to claim 1, wherein the reaction in step 1) is conducted at 0° C. to 100° C.

5. The method according to claim 1, wherein the alkali in step 2) is selected from the group consisting of: potassium tert-butoxide, sodium tert-butoxide, sodium methoxide, sodium ethoxide, lithium N,N-diisopropylamide, sodium hydride, sodium amide, lithium hexamethyldisilazide (LiHMDS), sodium hexamethyldisilazide (NaHMDS), potassium hexamethyldisilazide (KHMDS), 1,8-diazadispiro[5.4.0]undec-7-ene, 1,1,3,3-tetramethylguanidine, N,N-diisopropylethylamine (DIPEA), triethylamine (TEA), pyrrolidine, piperidine, and morpholine.

6. The method according to claim 1, wherein a solvent used in step 2) is selected from the group consisting of: tetrahydrofuran (THF), dioxane, DMF, dimethyl sulfoxide (DMSO), N-methylpyrrolidone (NMP), N,N-dimethylacetamide (DMAC), and acetonitrile.

7. The method according to claim 1, wherein in step 2), an amount of the 1-(2-methyl-2H-tetrazol-5-yl) ethanone is 0.5 to 2.0 equivalents of an amount of the intermediate shown in formula (II).

8. The method according to claim 1, wherein the ammonia source in step 2) is: ammonia water, a solution of ammonia in methanol, ammonium acetate, ammonium chloride, ammonium sulfate, ammonium carbonate, or ammonium bicarbonate.

9. The method according to claim 1, wherein in step 2), an amount of the ammonia source is 5.0 to 10.0 equivalents of the amount of the intermediate shown in formula (II).

10. The method according to claim 1, wherein the one-pot synthesis in step 2) is conducted at −10° C. to 100° C.

11. An intermediate of formula II:

II

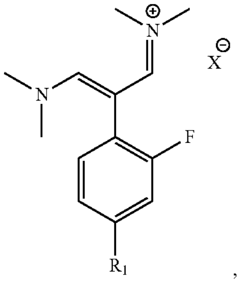

, wherein R1 is selected from the group consisting of: nitro, benzyloxycarbonylamino, chlorine, bromine, iodine, trifluorosulfonyloxy, methanesulfonyloxy, benzenesulfonyloxy, p-toluenesulfonyloxy, and carboxylate, and $X^{\ominus}$ is selected from the group consisting of: a tetrafluoroborate ion, a perchlorate ion, and a hexafluorophosphate ion; and wherein said intermediate is prepared by a method comprising the following steps:

subjecting 2-fluoro-4-substituted phenylacetic acid to a reaction with a Vilsmeier reagent, and adding a resulting reaction solution to an MX aqueous solution for quenching to obtain the intermediate shown in formula (II):

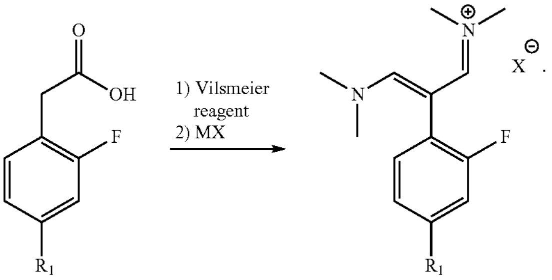

II wherein the MX is selected from the group consisting of: sodium tetrafluoroborate, potassium tetrafluoroborate, sodium perchlorate, sodium hexafluorophosphate, and potassium hexafluorophosphate.

12. The intermediate according to claim 11, wherein the Vilsmeier reagent is a combination of: N,N-dimethylformamide (DMF) and phosphorus oxychloride, DMF and oxalyl chloride, or DMF and thionyl chloride.

13. The intermediate according to claim 11, wherein an amount of the MX is 1 to 3 equivalents of an amount of the 2-fluoro-4-substituted phenylacetic acid.

14. The intermediate according to claim 11, wherein the reaction is conducted at 0° C. to 100° C.

* * * * *